(12) United States Patent
Schoo et al.

(10) Patent No.: US 8,188,485 B2
(45) Date of Patent: May 29, 2012

(54) DETECTION SYSTEM HAVING A LIGHT EMITTING DIODE

(75) Inventors: Harmannus Franciscus Maria Schoo, Eersel (NL); Jacobus Johannes Frederik Van Veen, Badhoevedorp (NL); Hermanus Hendricus Petrus Theodorus Bekman, Purmerend (NL)

(73) Assignee: Nederlandse Organisatie voor toegepast-natuurwetenschappelijk Onderzoek TNO, Delft (NL)

( * ) Notice: Subject to any disclaimer, the term of this patent is extended or adjusted under 35 U.S.C. 154(b) by 52 days.

(21) Appl. No.: 10/561,261

(22) PCT Filed: Jun. 17, 2004

(86) PCT No.: PCT/NL2004/000432
§ 371 (c)(1),
(2), (4) Date: Feb. 10, 2006

(87) PCT Pub. No.: WO2005/001945
PCT Pub. Date: Jan. 6, 2005

(65) Prior Publication Data
US 2006/0138447 A1      Jun. 29, 2006

(30) Foreign Application Priority Data
Jun. 17, 2003   (NL) ..................................... 1023679

(51) Int. Cl.
*H01L 27/15* (2006.01)
(52) U.S. Cl. .................. 257/79; 257/E33.076; 257/103; 257/40; 257/E51.001
(58) Field of Classification Search .................... 257/40, 257/103
See application file for complete search history.

(56) References Cited

U.S. PATENT DOCUMENTS

| | | | | |
|---|---|---|---|---|
| 4,119,949 A | * | 10/1978 | Lindgren | 340/630 |
| 5,307,146 A | | 4/1994 | Porter et al. | |
| 5,946,550 A | * | 8/1999 | Papadimitrakopoulos | 438/99 |
| 5,965,887 A | * | 10/1999 | Patton | 250/339.09 |
| 6,002,477 A | * | 12/1999 | Hammer | 356/307 |
| 6,127,693 A | | 10/2000 | Chen et al. | |
| 6,235,414 B1 | * | 5/2001 | Epstein et al. | 428/690 |
| 6,278,134 B1 | * | 8/2001 | Capasso et al. | 257/96 |
| 6,331,438 B1 | | 12/2001 | Aylott et al. | |

(Continued)

FOREIGN PATENT DOCUMENTS

EP        0462755 A1    12/1991

(Continued)

OTHER PUBLICATIONS

Dickert et al, "Solvatochromic betaine dyes as optochemical sensor materials: detection of polar and non-polar vapors," Sensors and Actuators B, 70, (2000), 263-269.*

(Continued)

*Primary Examiner* — Anthony Ho
(74) *Attorney, Agent, or Firm* — Swanson & Bratschun, L.L.C.

(57) ABSTRACT

The invention relates to a light emitting diode having at least one (semi)conductive electroluminescent active layer which comprises at least two different electroluminescent functionalities, wherein the emission spectrum of the diode exhibits at least two intensity maxima. The invention further relates to a detector which comprises a light emitting diode which is capable of emitting light at least two mutually separate intensity maxima.

33 Claims, 7 Drawing Sheets

U.S. PATENT DOCUMENTS

| | | | |
|---|---|---|---|
| 2002/0017612 A1* | 2/2002 | Yu et al. | 250/370.11 |
| 2002/0071963 A1* | 6/2002 | Fujii | 428/690 |
| 2002/0121638 A1* | 9/2002 | Grushin et al. | 257/40 |
| 2002/0190250 A1* | 12/2002 | Grushin et al. | 257/40 |
| 2005/0030545 A1* | 2/2005 | Tuschel et al. | 356/454 |

FOREIGN PATENT DOCUMENTS

| | | | |
|---|---|---|---|
| EP | 1286569 A1 * | 2/2003 | |
| GB | 2340304 A * | 2/2000 | |
| JP | 07030148 | 1/1995 | |

OTHER PUBLICATIONS

Arias et al, "Doped conducting-polymer—semiconducting-polymer interfaces: Their use in organic photovoltaic devices," Physical Review B, vol. 60, No. 3, 1999, 1854-1860.*
Paik et al. (2002) Macromolecules, 35:6782-6791.
Welter et al. (Jan. 2003) Nature 42:54-57.
Zhang and Heeger (Aug. 1998) Journal of Applied Physics, 84(3):1579-1582.

* cited by examiner

DETECTION SYSTEM HAVING A LIGHT EMITTING DIODE

RELATED APPLICATIONS

This application is a 35 U.S.C. §371 national phase application of International PCT Application Serial Number PCT/NL2004/000432 (WO 2005/001945), filed on Jun. 17, 2004, entitled "Light Emitting Diode", which application claims priority to Netherlands patent application serial number 1023679, filed Jun. 17, 2003, both of which are incorporated herein by reference in their entirety.

The invention relates to a light emitting diode, to a method of manufacturing such a diode and to the use of a single light source, such as a light emitting diode according to the invention, for generating a reference signal and a detection signal in a detection system, in particular a sensor.

The invention further relates to a detection system that comprises a light emitting diode which is capable of emitting light at at least two mutually separate intensity maxima.

Photospectroscopic detection techniques, such as UV-VIS absorption detection, infrared (IR) spectroscopy, fluorescence detection, etc., are much used in analytic chemistry.

By contacting a sample that is present in an analysis channel (for instance a cuvette, a flow-through cell or a surface, such as a selective coating, on which it is immobilized) with light in a particular wavelength range and measuring the changes in intensity between the emitted light ($I_0$) and the intensity (I) of the light after contact with the sample (e.g. directly on the sample or indirectly via a coating on which the sample is immobilized), the presence of particular substances in the sample can be determined qualitatively and/or quantitatively.

Usually, light is generated by means of a light source with only one dominant intensity maximum in the emission spectrum, such as light emitting diodes (LEDs). LEDs generally emit light of a relatively narrow wavelength range, and hence are generally to a large extent monochromatic (emit light of a particular color). These features of LEDs are generally regarded as favorable, because of the positive effect of these features on the accuracy, greater signal to noise level, greater sensitivity and hence greater dynamic range and selectivity of the detection system.

For a highest possible accuracy, and for a largest possible dynamic measuring range, it is desired to measure at a wavelength that corresponds to an absorption maximum of the substance or substances to be measured. For a good selectivity, it is desired to selectively contact light in a narrow wavelength range with the substance(s) to be measured and/or to selectively measure changes of light intensity in a narrow wavelength range. Often, filters, grating, prisms and the like are used to select a narrow wavelength range (for instance 2-20 nm).

During the light intensity measurement, disturbances may arise in the measured signal, in particular as a result of changes in the measuring environment (such as change of temperature and/or moisture content, ambient light penetrating the measuring system and/or electromagnetic radiation from the environment influencing the measured signal), changes in the detection system (such as changes in the emitted light intensity) and variations in the optical properties of the sample (for instance undesired light absorption due to contaminations in the sample, variable scattering as a result of the presence of air bubbles or small particles and/or changes in the refractive index). As a result, the noise in the measured signal increases and the detection limit for a particular substance decreases.

To render detection systems, such as sensors, less sensitive to such disturbances, often use is made of a reference signal. Such a signal is used in particular in absorption measurements. With it, disturbing background signals can be eliminated or at least be reduced. The reference signal is usually guided through a second channel (the reference channel), which differs from the sample channel in that the substances to be measured are absent. The measurement of the reference signal is often done with a different light source with different spectral characteristics. By the use of a reference channel, measuring accuracy can be improved.

Compared with a detection system without reference signal, there may be some improvement in the sensitivity to scattered light, ambient light, electromagnetic disturbances, temperature and/or moisture, but it has been found that there is good chance of problems indeed, in that the light source of the reference channel reacts differently than the light source for measuring the light of the analysis channel, for instance to temperature changes, moisture content changes. In addition, the life and/or power of the light source may be different.

It is an object of the present invention to provide a new light source, which can serve as an alternative to a known light source, in particular for use in a detection system, in particular a sensor, having at least a signal channel and a reference channel.

It has now been found that this object is realized by a new type of LED with a particular emission spectrum, in particular a LED with an electroluminescent layer in which one or more electroluminescent organic compounds are present.

The invention accordingly relates to a light emitting diode having at least one (semi)conductive electroluminescent active layer which comprises at least two different electroluminescent functionalities, wherein the emission spectrum of the diode exhibits at least two intensity maxima, in particular at least two dominant intensity maxima. A dominant intensity maximum is herein understood to mean a maximum of a peak in the emission spectrum which comprises at least 5% of the total emission in the emission spectrum. Preferably, at least one peak comprises 25-75% of the total emission, and more preferably there are at least two peaks each comprising 25-75% of the total emission, with the sum of the two emissions being 100% at a maximum.

More specifically, the invention relates to a light emitting diode having at least one (semi)conductive electroluminescent active layer which comprises at least two different electroluminescent functionalities, wherein the emission spectrum of the diode exhibits at least two intensity maxima, in particular at least two dominant intensity maxima, and wherein the active layer comprises at least one electroluminescent organic compound.

A LED according to the invention is a diode with an active layer which is (semi)conductively in communication with two electrodes. The active layer is electroluminescent, that is, at a sufficiently high potential difference (for instance approximately 2V) across the electrodes, photons are generated of a wavelength in the UV, VIS or IR range.

With respect to the emission spectrum, what is meant here is the light emission spectrum in the range of UV light up to and including IR light in particular between 190 and 1500 nm, preferably between 350 and 1000 nm, more preferably from 400 to 800 nm.

A wavelength at which an intensity maximum occurs is herein called $\lambda_{max}$.

Sensitivity of a detection system, such as a sensor, is the extent to which the measured signal changes upon a particular change in the concentration or amount of the substance to be detected.

The detection limit is the lowest measurable concentration or amount of a substance. It is determined by the signal to noise ratio. In general, the detection limit for a particular substance is reached at a signal to noise ratio of 2 (if the noise is represented as peak to peak) or 4 (if the noise is represented as the root of the mean square noise (RMS noise)).

Stability is the extent to which a system is resistant to changes in the detection system, influences from the sample and influences from the environment. According as a system is more stable, the noise will be less and/or fewer artifacts will occur in the measuring signal, such as spikes, base line drift and/or base line shifts.

It has been found that a LED according to the invention is very suitable for use in an optical detection system, for instance a UV-VIS absorption meter. In principle, more wavelengths on or near various $\lambda_{max}$ can be used as detection wavelength (detection signal).

A particular advantage of a LED according to the invention is the possibility of selecting from a single light source two different wavelengths on or near two different intensity maxima, which are spectrally far apart, so that one intensity maximum coincides with, or is at least in the vicinity of, the maximum in an absorption peak of the substance to be measured, and the other intensity maximum preferably falls as far as possible outside the absorption peak or in the isobestic point. Preferably, one wavelength serves as reference signal and a second wavelength serves as detection signal. It has been found that such a detection system has a very good stability, for instance upon fluctuations in the supply current, the intensity of the ambient light, electromagnetic disturbances, the temperature and/or the air humidity.

It has also been found that a detection system, such as a sensor system, utilizing such a LED light source according to the invention has a good stability upon fluctuations in the current supply and/or ageing of the light source.

A LED according to the invention is particularly suitable for use in a detection system, such as a sensor system, in which the reference signal and the detection signal are guided through the same analysis channel and hence the reference signal comes into contact with the same sample channel as the detection signal. Here, preferably, a reference signal is selected of a wavelength which is not absorbed, or much less so, by the sample. Thus, it has been found that it is possible to further increase the stability of the measuring system. It is supposed that this is connected with the elimination, or at least reduction, of the influence of changes in the sample (such as refractive index changes and/or disturbances resulting from the presence of air bubbles and/or small particles).

A LED according to the invention is particularly suitable for use ill a miniaturized sensor system, as in a sensor system integrated on a chip.

FIG. 1 schematically shows a LED according to the invention.

FIG. 2 schematically shows an emission spectrum of a LED according to the invention.

FIGS. 3A-3G schematically show embodiments of sensor systems according to the invention.

FIG. 4C moreover shows a photoluminescence spectrum (PL).

Very good results have been achieved with a bimodal LED, i.e. a LED which has exactly two $\lambda_{max}$ in the emission spectrum. Such a LED has been found very suitable for use as a single light source for providing both a reference signal and a detection signal in a detector.

Preferably, the difference in wavelength between two consecutive $\lambda_{max}$ is at least as large as the width of the absorption peak of the substance on which measurements are made. Good results have been attained, for instance, with a LED where the difference between two consecutive $\lambda_{max}$ is at least 50 nm, and in particular with a LED where this difference is at least 100 nm. The maximum difference between two consecutive $\lambda_{max}$ is not particularly critical. Very good results have been obtained, for instance, with a LED where this difference is less than 1200 nm, more particularly 400 nm or less.

Preferably, the emission spectrum of the LED shows a first maximum in the top of an absorption peak of a sample to be measured and a second maximum in or beyond a flank (viewed from $\lambda_{max}$) of the absorption peak of a sample to be measured. More preferably, the second maximum is situated wholly next to the absorption peak, and particularly preferably has a wavelength greater than the wavelength at which the absorption maximum occurs.

Preferably, a LED according to the invention has an intensity ratio between two consecutive maxima in the emission spectrum in the range of 0.5 to 1. Such a LED is particularly suitable to generate both a reference signal and a detection signal for an optical detector.

Figure 2:
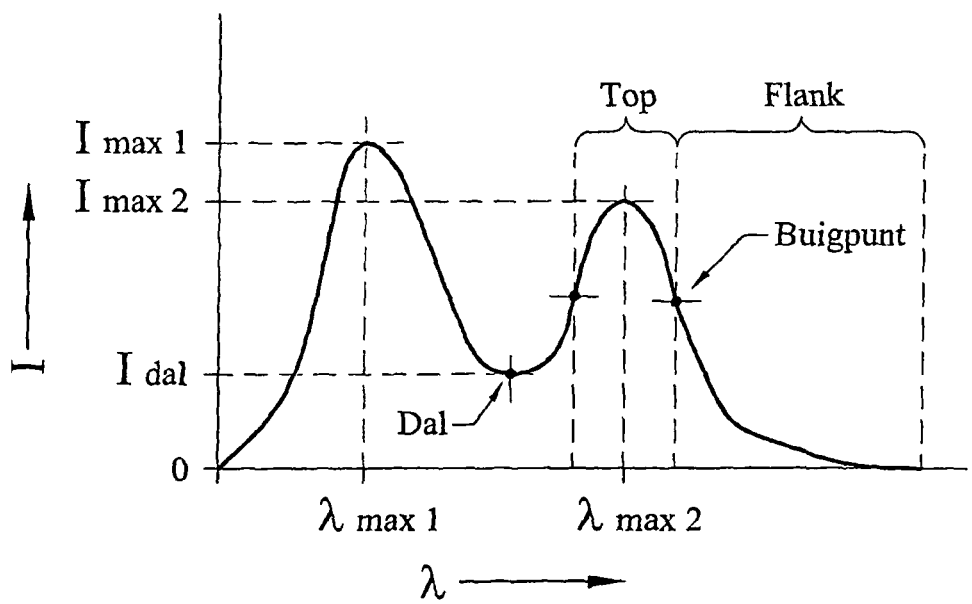

Preferably, a LED according to the invention has an emission spectrum in which the peak-to-valley ratios ($I_{max}/I_{valley}$) of two maxima have a value from 2 to infinite, and in particular from 10 to infinite. The peak-to-valley ratio of a maximum is herein the ratio between the intensity at a $\lambda_{max}$ (in FIG. 2: $I_{max1}$ or $I_{max2}$) and the minimal intensity ($I_{valley}$, see also FIG. 2) between the two $\lambda_{max}$ of two maxima (in FIG. 2: $I_{max1}$ and $I_{max2}$). Such a LED is particularly preferred in view of the detection limit of a system in which such a LED is used.

The LED must meet a number of properties. Photons need to be generated at at least two different wavelengths, when a sufficiently high electrical potential (for instance 2 Volts or more) is applied across the layer, the layer should be sufficiently electrically conductive and the layer should be sufficiently transparent at least to the at least two different wavelengths whose emission is desired. The skilled person will be able to select suitable materials, ratios between the different constituents and other parameters on the basis of system specifications, general knowledge of the art and what is described herein.

The generation of photons at at least two different wavelengths is preferably effected directly in the photoactive layer, by choosing the electroluminescent functionalities in the layer such that at least two intensity maxima occur in the emission spectrum.

A LED according to the invention can comprise a continuous or a segmented photoactive layer.

A continuous photoactive layer is herein understood to mean a layer which can emit essentially the complete spectrum from essentially any point of the photoactive layer, such as a photoactive layer which comprises a mixture of electroluminescent compounds or a compound having more electroluminescent functionalities.

Figure 5A:
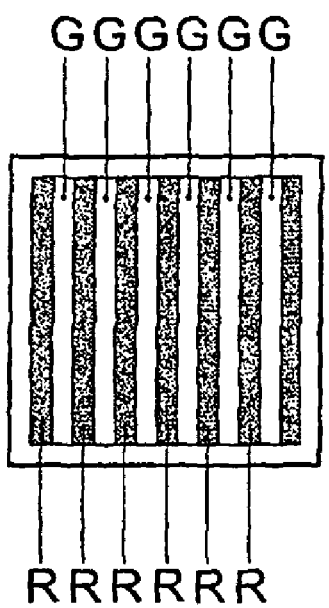
FIGS. 5A and 5B show two examples of segmented LEDs according to the invention.
Figure 5B:
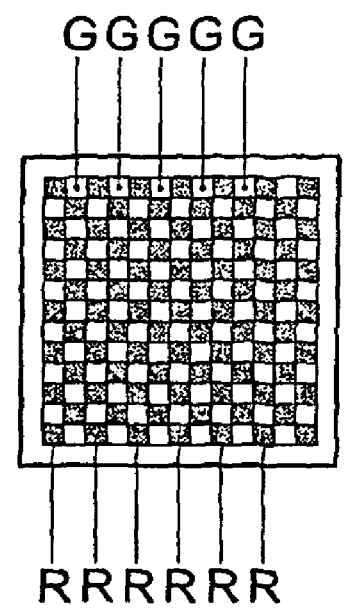

A segmented photoactive layer is understood to mean a layer which is divided up into at least segments, with at least two segments having a mutually different emission spectrum. The different segments can have a monomodal emission spectrum having a mutually different $\lambda_{max}$. Examples of segmented LEDs are represented in FIG. 5A (with strips) and FIG. 5B (with pixels). "R" and "G" herein indicate the different colors. The photoactive layer may furthermore be segmented in that the different segments are stacked. The photoactive layer then in fact comprises a number of sublayers having different electroluminescent functionalities in the different sublayers.

The width and height of the pixels, and the width of the strips, respectively, are not particularly critical and can for instance be chosen very suitably in the range of from 100 nm to 500 µm, more preferably from 1 µm to 100 µm.

In addition, or instead, it is possible, by the use of one or more filters, to ensure that the LED emits photons effectively, so that the wavelength spectrum exhibits at least two maxima, by providing the LED with one or more filters that selectively pass, or stop, particular wavelengths, for instance by using a filter that is selectively not transmissive to photons in a particular band of the emission spectrum (a so-called "notch" filter or band-stop filter). Such filters are known per se and commercially available. Examples include Schott filters, which are sold, e.g., by Newportlab (Cino, Calif., USA; www.newportlab.com/schott.htm). Thus, the invention also relates to a LED having at least one (semi)conductive electroluminescent active layer which under a sufficiently high electrical voltage emits light of at least two different wavelengths, while the emission spectrum of the diode exhibits at least two intensity maxima, and said maxima have been obtained through the use of at least one filter, in particular a notch filter.

Suitable materials having an electroluminescent functionality are known per se and can be selected from the group of inorganic and organic electroluminescent compounds.

The suitable inorganic materials include (nano) particles which exhibit a bandgap and hence have emitting properties. Such materials are known in the art. The suitable materials include inter alia phosphors and quantum dots.

Particularly suitable compounds having an electroluminescent functionality are organic electroluminescent compounds, such as electroluminescent polymers, electroluminescent oligomeric compounds (for instance oligomeric dyes) and electroluminescent single compounds (for instance electroluminescent dyes).

Oligomers are herein understood to be molecules built up from 2-9 monomeric units.

Polymers are herein understood to be molecules built up from more than 9 monomeric units.

Single compounds are herein understood to be compounds which, in contrast to oligomers and polymers, are not built up from repetitive units (monomeric units). Examples of such compounds are monomers and other non-polymerized molecules with conjugated bonds. Often, such compounds have a relatively low molecular weight compared with polymers, for instance a molecular weight of 100-20,000 g/mol.

With a view to the manufacture of a microsystem, for instance by means of printing, it has been found that the use of a soluble polymer as electroluminescent compound is of advantage. A composition with an electroluminescent polymer has been found to be printable particularly well.

Very good results have been achieved inter alia with a LED in which at least one of the electroluminescent compounds is selected from the group consisting of polyphenylene compounds, poly(paraphenylene vinylene) compounds, polyfluorene compounds, polyacetylene compounds, polythiophene compounds, polypyrroles, polyanilines, including derivatives of these polymers (in particular alkyl, aryl and alkoxy derivatives), copolymers of these polymers and the above polymers which have been derivatized with one or more of the dyes mentioned herein.

An important advantage of such polymers is that they are not only electroluminescent but also (semi)conductive. In addition, these polymers have been found to be relatively easily processable, for instance by spin coating or printing. Also, the mechanical properties of a layer having one or more of these polymers in the LED have been found to be good.

Polyphenylenes are suitable, for instance, for generating blue light.

Particularly preferred are poly(paraphenylene vinylene) derivatives, such as homopolymers and copolymers comprising a group represented by Formula 1

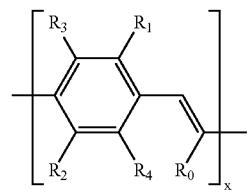

Formula 1 wherein x is preferably chosen in the range of from 10 to 1,000,000, more preferably from 100 to 1,000, wherein each $R_0$, $R_1$, $R_2$, $R_3$ and $R_4$ are preferably each selected independently from the group consisting of (hereinafter referred to as R groups):

H branched and unbranched alkyl groups of the formula $-C_aH_{2a+1}$, branched and unbranched alkoxy groups of the formula $-O-C_aH_{2a+1}$, aryl groups (optionally substituted with one or more alkyl groups and/or one or more alkoxy alkyl groups, preferably of the formula $-C_aH_{2a+1}$, and $-O-C_aH_{2a+1}$, respectively, as described above), preferably aryl groups having 6 to 12 carbon atoms in the ring structure $C\equiv N$ In Formula 1 "a" is preferably chosen in the range of from 1 to 20 and more preferably in the range of 2-10.

An advantage of polyphenylene compounds and in particular poly(paraphenylene vinylidene) compounds is the multitude of possibilities of influencing the $\lambda_{max}$ through derivatization. Green/yellow light can be generated, for instance, from a compound according to Formula 1 in which each $R_0$ through $R_4$ represents hydrogen. Yellow light can be generated with a compound in which one of $R_1$-$R_4$ represents alkyl, aryl or alkoxyalkyl and the other R groups represent hydrogen. Orange light can be obtained from a compound in which two of $R_1$-$R_4$, preferably $R_1$ and $R_2$, represent an alkyl, aryl or alkoxyalkyl and the others hydrogen. A further shift towards red light can be obtained through a compound in which two of $R_1$-$R_4$, preferably $R_1$ and $R_2$, represent an alkyl, aryl or alkoxyalkyl and $R_0$ is $-C\equiv N$.

Particularly preferred are, furthermore, polyfluorene derivatives such as homopolymers and copolymers which comprise a group which is represented by Formula 2.

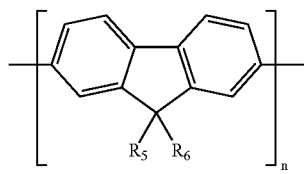

Formula 2 wherein n is preferably chosen in the range of from 10 to 1,000,000 and more preferably from 100 to 200,000, wherein each $R_5$ and $R_6$ are each preferably chosen independently from the R groups as defined for Formula 1.

Particularly suitable as oligomeric dye is a compound which can be represented by Formula 1 or 2, wherein x and n, respectively, is 2 to 10 and the various R's are as described above. Another oligomer that can be used is an oligothiophene, preferably an oxidized oligothiophene as shown in Formula 3.

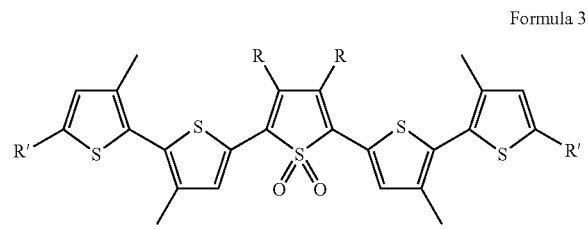

Formula 3 wherein each R and R' are preferably selected independently from the R groups as defined for Formula 1.

With regard to the single dyes, good results have been obtained inter alia with a compound according to Formula 4.

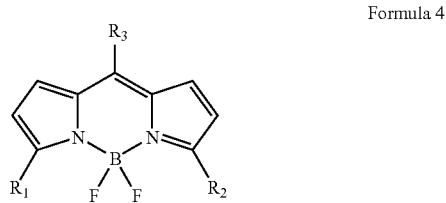

Formula 4 wherein $R_1$, $R_2$ and $R_3$ are preferably each selected independently from the R groups as defined for Formula 1.

Such a compound has been found, in a LED, to have a relatively narrow emission band, experienced as favorable, for instance in comparison with a number of electroluminescent polymers.

In addition, such a compound has been found to have a very good stability in a LED.

The different electroluminescent functionalities can be provided for in a variety of ways. Highly suitable, for instance, is an active layer in which at least two electroluminescent compounds are present having a different maximum in the emission spectrum. These compounds may be mixed with each other. Preferably, the compounds are homogeneously mixed, so that the active layer consists substantially of one single phase, which is preferably amorphous.

Thus, good results have been obtained, for instance, with a LED in which, as different electroluminescent functionalities, two or more polymers are present having a different $\lambda_{max}$, as for instance two polymers from the same class (for instance two polyparaphenylene vinylene derivatives) or two polymers from different classes (for instance a polyparaphenylene vinylene derivative and a polyfluorene derivative).

The invention further relates to a LED in which the active layer comprises at least one electroluminescent polymer, as described above, and at least one other electroluminescent compound, such as an oligomer or single compound. Examples include LEDs in which the active layer comprises a polymeric compound according to Formula 1 or 2 and further a compound according to Formula 4 or 5 or an oligomeric compound according to Formula 1, 2 or 3.

In the light of the invention, it is possible that the active layer comprises only oligomeric and/or single compounds as electroluminescent compounds. These may for instance be embedded in a (semi)conductive matrix, for instance a (semi) conductive polymer. If the intrinsic conductivity of one or more of these oligomeric and/or single compounds is sufficient, the compounds without the (semi)conductive matrix can form the LED, along with the electrodes.

The invention further relates to a LED in which the two different electroluminescent functionalities form part of one electroluminescent compound, in particular one organic compound. Such a compound can for instance be a polymer, preferably a block copolymer or a graft copolymer, having at least two different electroluminescent segments. The compound can be an electroluminescent polymer which has been derivatized with at least one electroluminescent dye. Another example is a non-electroluminescent compound, preferably a polymer, which has been derivatized with at least two different electroluminescent dyes. Preferred is an electroluminescent compound having at least two different electroluminescent functionalities at least partly formed by at least two electroluminescent polymers, oligomers and/or single compounds as have been described hereinabove. Examples of such compounds are block copolymers and graft polymers of polyparaphenylene vinylene) derivatives, polyfluorene derivatives and combinations thereof.

The proportion in which the different electroluminescent functionalities are present depends on the desired LED specifications and the properties of the material, in particular the molar intensity at $\lambda_{max}$. The skilled person will be able to determine suitable proportions on the basis of general knowledge.

Figure 1:
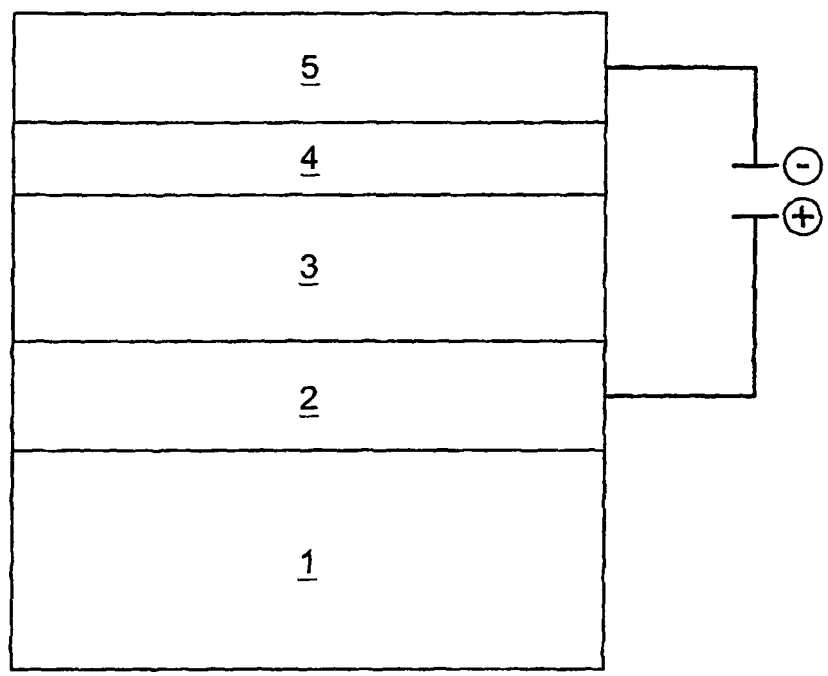

FIG. 1 schematically shows a diode according to the invention in which a (semi)conductive electroluminescent active layer 104 is present between two electrodes 102 and 105. As positive and as negative electrode, materials can be used which are known per se for use in diodes, in particular in diodes in which the active layer is based on a semiconductive polymer. A very suitable material as positive electrode is a metal oxide, for instance indium tin oxide (ITO), tin oxide, zinc oxide.

A very suitable material as negative electrode is a low work function metal, for instance calcium, lithium, aluminum, silver, barium or ytterbium, as well as alloys thereof. Lithium and aluminum are suitable in particular in the form of an Li—Al alloy. Silver and barium are suitable in particular in the form of a multilayer system, at least comprising a barium layer and a silver layer.

These three parts in effect constitute the diode. Usually, these parts will be present on a carrier material 101. This carrier material can be, for instance, a glass or a plastic having a sufficient transparency to photons of a wavelength on or near at least two $\lambda_{max}$ of the LED. The carrier material can serve as light guide (waveguide) for the light to the sample and optionally to the measuring sensor(s) (e.g. measuring diode(s)). Further, between the different parts one or more further layers may be present, such as a buffer layer 103 which contributes to the hole injection and/or provides for a more planar transition (interface) between the positive electrode 102 and the active layer 104. Very suitable as a buffer layer 103 is, for instance, polyethylene dioxythiophene (PEDOT), which is able to contribute both to a better hole injection and to a more planar interface. A filtering layer (not drawn) can be present on the carrier material or somewhere between the carrier material and the photoactive layer.

The skilled person will be able to choose suitable materials and layer thicknesses on the basis of the desired system specifications. Of importance here is that the layers through which the light produced in the active layer is to pass, be sufficiently transparent to photons of the desired wavelengths (viz. on or near at least two $\lambda_{max}$). With respect to the layer thicknesses, good results have been obtained, for instance, with a LED having a positive electrode 102 of a thickness of approximately 75-300 nm, having a layer 103 (such as a PEDOT layer) of approximately 100-400 nm, having an active layer of approximately 50-200 nm and/or a negative electrode 105 of a thickness of approximately 75-300 nm. Depending on the specifications, such as desired total thickness of the LED and desired light intensity at a particular voltage, one or more of the layers can have a greater or lesser thickness than those mentioned.

The various layers are preferably selected such that the surface resistance of the positive electrode and/or the negative electrode is less than 20Ω across the electrode surface.

The magnitude of the LED surface can be selected within a wide range, depending on the use. The surface area can be, for instance, 1 mm$^2$ or less, which is of interest in particular for use in microsensors. The lower limit is not particularly critical and can be 1 μm or less.

A LED can also be relatively large, for instance of from 1 mm$^2$ to 10 cm$^2$ or more. A larger surface is of interest inter alia for use in a miniaturized sensor system with more detection channels (see for instance FIG. 3C), for instance for the simultaneous detection of different components or for the detection of several samples at the same time. As a LED according to the invention can have a large surface, it is possible, also in a system having large numbers of detection and possibly reference channels (an array of sensors), to make use of a single light source for many channels, which is favorable for the stability of the measurement. A large LED surface is furthermore desired in a system for measuring an overall concentration/amount instead of a local concentration.

The invention further relates to a method for manufacturing a LED, in particular to a method in which at least one active layer, which comprises at least one electroluminescent compound as has been described above, is applied to an electrode. The skilled person will be able to choose a suitable manufacturing technique on the basis of what is described herein, general knowledge and literature in the field of the manufacture of monomodal LEDs with a comparable electroluminescent material. A suitable manufacturing technique can be based, for instance, on a method as described in WO 03/026011, WO03/022581 or WO 02/082561.

A particularly suitable method for this purpose is spin coating of a solution in which one or more electroluminescent compounds are present. A suitable solvent can be routinely determined by the skilled person, depending on the electroluminescent material and the coating technique. Good results have been achieved inter alia with toluene, in particular in the manufacture of a LED having a polyparaphenylene vinylene in the active layer.

A very suitable technique to apply one or more layers is printing, which enables relatively simple manufacture of an array of sensors on the basis of different materials. Printing is eminently suitable for manufacturing miniaturized systems.

Preferably, a LED according to the invention is manufactured by applying to a substrate that is transparent at the various $\lambda_{max}$ a layer that forms the first electrode, for instance a metal oxide such as ITO. This layer can be applied with a technique known per se. Very suitable is sputtering. The buffer layer 103 can be applied with a technique known per se.

Spin coating is very suitable, for instance, for applying a polymeric buffer layer 103 such as PEDOT. The active layer can be applied to the electrode 102 or the buffer layer 103 as described hereinabove. The second electrode can be applied to the active layer with a technique known per se. A metal, such as calcium, can for instance be applied very well with vacuum deposition.

The invention furthermore relates to a detector, such as a sensor, that includes a LED which can emit photons of different wavelengths, such as a LED which is herein described having two different electroluminescent functionalities, so that the LED emits photons of different wavelengths simultaneously, while the emission spectrum exhibits two maxima. In principle, the LED can be used in any type of spectrophotometer, for instance for UV absorption, VIS absorption, IR absorption, fluorescence, surface plasma resonance (SPR), refractometry, an optochemical sensor and the like.

In addition, the invention relates to a detector comprising a light emitting diode which comprises at least one (semi) conductive electroluminescent active layer and which light emitting diode, depending on the direction of the electric current through the active layer, emits light having a first intensity maximum or, conversely, light having a second intensity maximum different from the first intensity maximum. Such a LED is known, for instance, from Nature, Vol 421, pp. 54-57 (2002). Thus, by using the LED under alternating voltage, alternately a reference signal and a detection signal can be generated, whereby advantages regarding the accuracy, the stability and the dynamic range of the detector can be realized comparably to a LED according to the invention.

A LED according to the invention is very suitable for use in a miniaturized detection system, such as a sensor on a chip. Schematic representations of such sensors are shown in FIGS. 3A-3F. The operation of the detector can be of transmissive (see FIGS. 3A, 3B 3D) or reflective (see FIGS. 3E and 3F) type. Also, it is possible to combine a number of detection units on one chip (FIG. 3C).

Figure 3A:
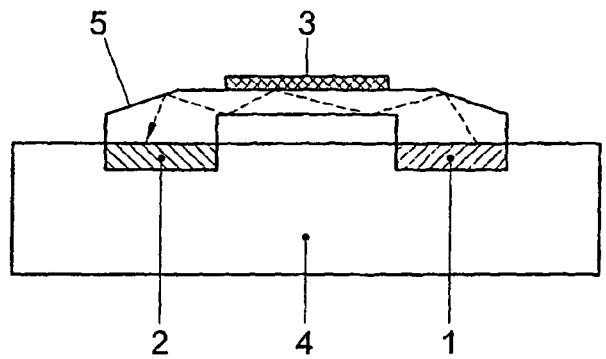
Figure 3B:
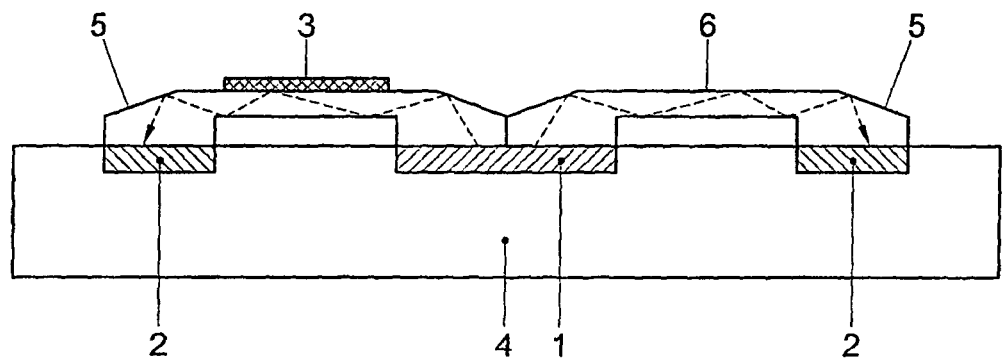
Figure 3C:
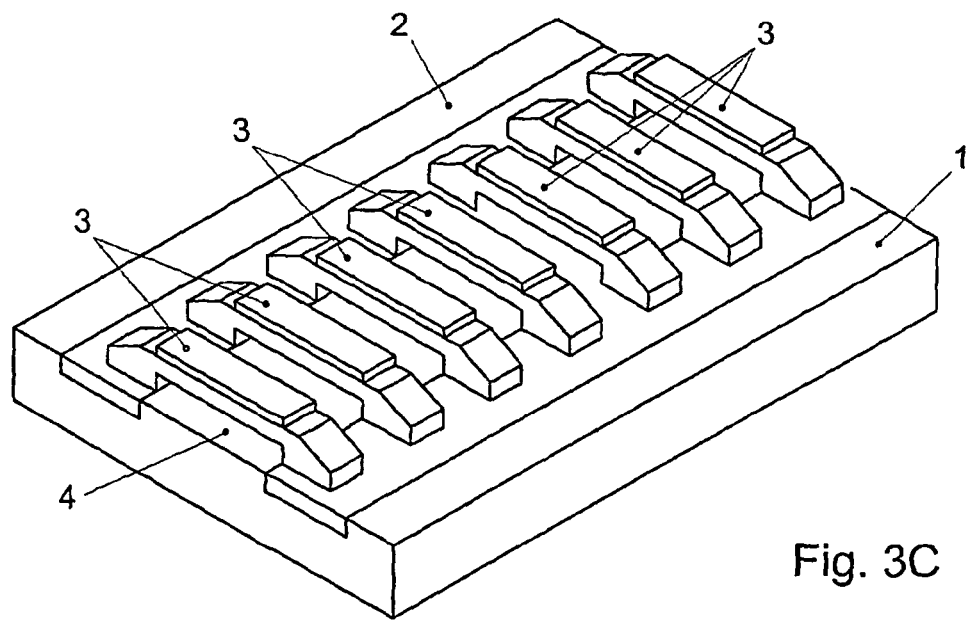
Figure 3D:
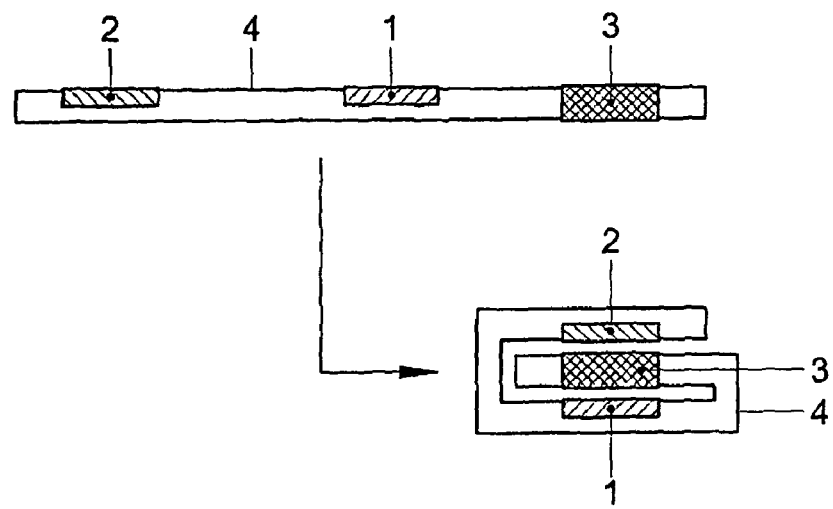
Figure 3E:
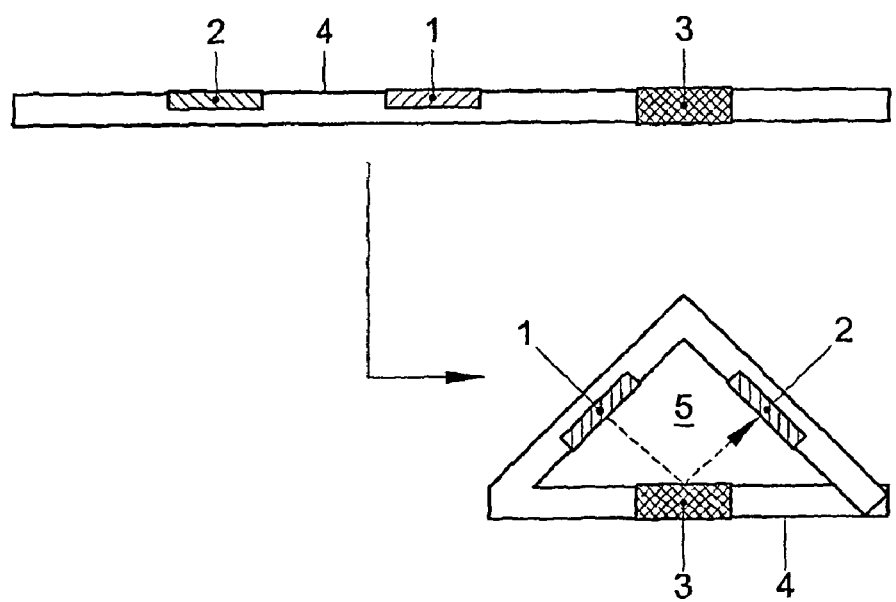
Figure 3F:
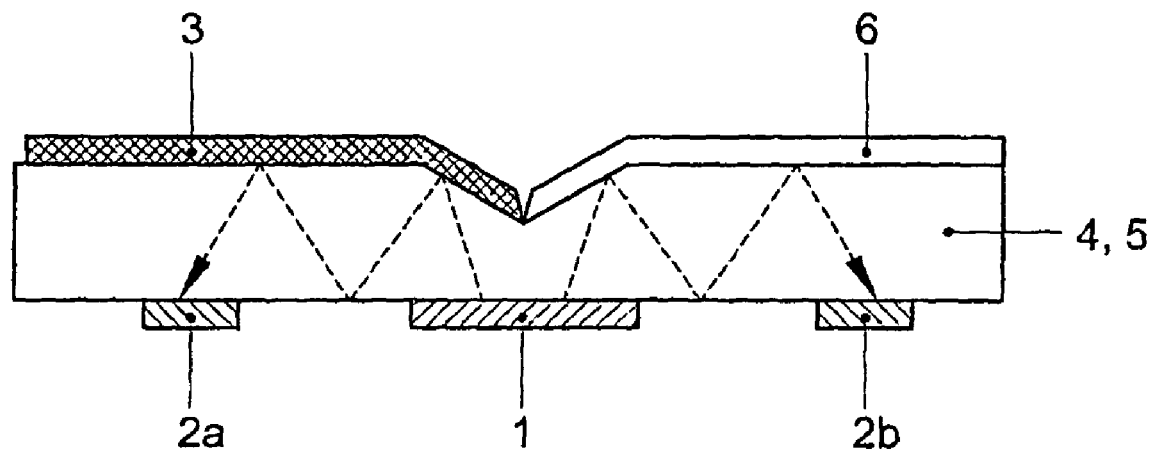
Figure 3G:
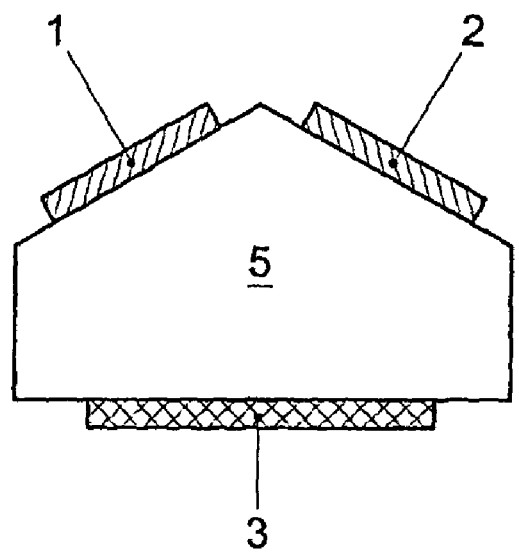

The sensor in FIGS. 3A-3G is formed by one or more LEDs 1, photodiodes 2 for measuring detection signal and reference signal, respectively, sample portions 3, in which or on which the sample is present during detection, and a carrier material 4, on which or in which the different sensor parts are fixed. Further, one or more light guides 5 may be present, which guide the light from the LED to the sample portion 3 and the detection diode 2a, and to a reference portion 6 and a reference diode 2b, respectively. Optionally, the function of carrier material 4 and light guide 5 may be combined (FIG. 3F). Optionally, the light guide 5 can be a prism around which the carrier material has been provided (FIG. 3E, prism is optional) or the prism can serve as carrier material and light guide (FIG. 3G).

The photodiodes can be, for instance, polymeric photodiodes. Such photodiodes are described, for instance, in Arias et al. Phys. Rev. B, 60(30), p 1854 (1999).

The sample portion can be, for instance, a cuvette with sample, a small transparent plate with sample, a flow-through channel through which sample can flow, or the environment itself. Such sample portions are known per se.

Preferably, the sample portion 3 comprises a coating by means of which one or more components to be measured can be subjected to an interaction, so that the absorption properties, fluorescence properties or refractive index of the coating change.

Suitable coatings are known per se.

A suitable coating for polar and non-polar vapors is described in "Solvatochromic betaine dyes as optochemical sensor materials: detection of polar and non-polar vapors" Dickert, F. L.; Geiger, U.; Lieberzeit, O.; Reutner, U. Sensors and Actuators B70 (2000), pp 263-269;

"Fiber-optic microsensor for high resolution pCO2 sensing in marine environment" Neurauter, G.; Klimant, I.; Wolfbeis, O. S. Fresenius J. Anal. Chem. (2000) 366, pp 481-487 describes a coating for carbon dioxide detection.

A coating for an ammonia sensor is known from "Sol-gel based optical sensor for dissolved ammonia" Lobnik, A.; Wolfbeis, O. S. Sensors and Actuators B51 (1998), pp 203-207.

As carrier material 4, for instance glass or plastic, for instance polyethylene or PET, is suitable. The carrier material can be a composite, such as a multilayer laminate.

In a preferred embodiment, the carrier material is flexible, so that it can be folded into a particular shape (see for instance FIGS. 3D and 3E).

Suitable as light guide is, for instance, glass or a transparent plastic such as polycarbonates, cyclic olefinic polymers (e.g. Zeonex®, Topas), polymethyl pentenes (e.g. TPX™), polymethyl methacrylates (PMMA), polystyrenes (PS), polyamides, polyvinyl chlorides, polyethyl terephthalates, polypropenes, styrene butadiene styrene copolymers, cellulose polymers, polyethylenes and polynorbornenes.

In such a use, the detection signal and the reference signal can both be directed at a composition to be analyzed, for instance a selective coating (see FIG. 3A, in which the reference diode (not drawn) is present next to or behind the detection diode, or in which the reference signal is measured without being guided through the sample (for instance FIGS. 3B, 3D).

In the case of an absorption measurement, the measuring wavelength typically corresponds to the absorption maximum of the substance to be measured (directly, or indirectly via binding to a selective coating). The reference wavelength is preferably in a region without relevant absorption. In the case of a fluorescence measurement (or of a fluorescent coating), preferably two components are excited (one component to be measured and a reference component). In the case where the sensor includes a selective coating to which the sample adheres, the measuring wavelength is used to excite the fluorophore that is sensitive to the component to be measured in the sample and the reference wavelength is used to excite a second fluorophore in the coating which, by contrast, is not sensitive to the component to be measured in the sample.

The invention further relates to the use of a single light source for generating a reference signal and a detection signal in a detector, in particular in a sensor, while the $\lambda_{max}$ of the reference signal differs from the $\lambda_{max}$ of the detection signal. Preferably, the light source is a LED as described herein, more preferably a bimodal LED as described herein.

The invention will now be illustrated in and by the following examples.

EXAMPLE 1

Manufacture of a LED

A glass carrier material was provided with a transparent layer of indium tin oxide (ITO) (commercially available e.g. from Baltzers) by means of sputtering to a layer thickness of ca. 150 nm and a surface resistance of maximally 20 Ω/square. On the ITO, a ca. 200 nm thick layer of PEDOT (Baytron P from Bayer) was applied by means of spin coating (1,000-3,000 rpm, 1 min. of drying at 180° C.).

Next, by means of spin coating, the electroluminescent layer, of ca. 100 nm, was manufactured. On the active layer, a calcium electrode layer of a thickness of ca. 150 nm was applied by means of vacuum deposition. The surface area of the LED was ca. 0.9 cm².

EXAMPLE 2

LED with Two poly(para-phenylene vinylene) Derivatives

A solution of two different poly(para-phenylene vinylene) derivatives, represented by the following formulae

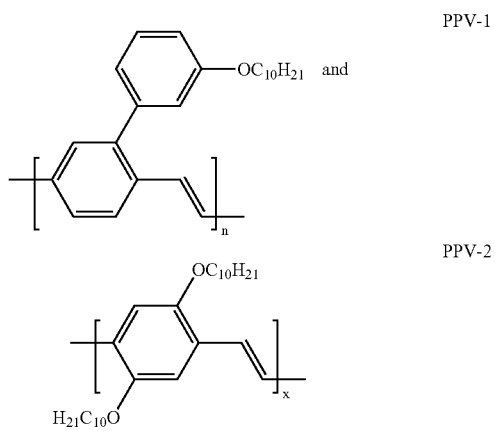

with a number-average molecular weight of 500 kD and 650 kD, respectively, was prepared by dissolving the two polymers in toluene at ca. 40° C. The total concentration of the two polymers was 0.5 wt. %.

This solution was used for spin coating the active layer in a LED as described in Example 1.

The LED was activated at 2 to 3 V and exhibited a $\lambda_{max}$ at 550 nm and at 590 nm, as determined with an Avantes Fiber optic spectrometer, type PC2000-ISA with 50 micron slit.

EXAMPLE 3

LED with poly(para-phenylene vinylene) Derivative and Polyfluorene Derivative

A solution of PPV-1 and a polyfluorene according to Formula 2 wherein $R_5$ and $R_6$ both represent n-$C_8H_{17}$ was prepared as described in Example 2.

Figure 4A:
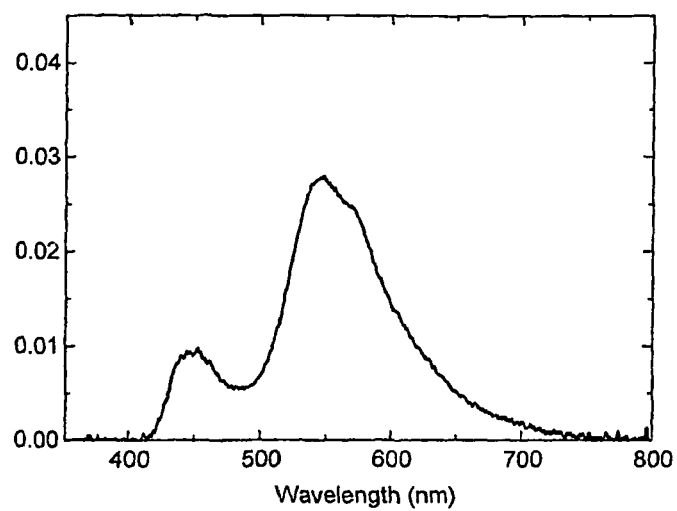
FIGS. 4A-4C show electroluminescence spectra (EL) of LEDs according to the invention.

The LED was activated at 4 V and exhibited a $\lambda_{max}$ at 460 nm and at 560 nm. The EL spectrum (determined as in Example 2) is represented in FIG. 4A.

EXAMPLE 4

Mixture of Single Dye and PPV-1

A solution in toluene was prepared from PPV-1 (0.5 wt. %) and a single dye (DYE-1, 0.005 wt. %)

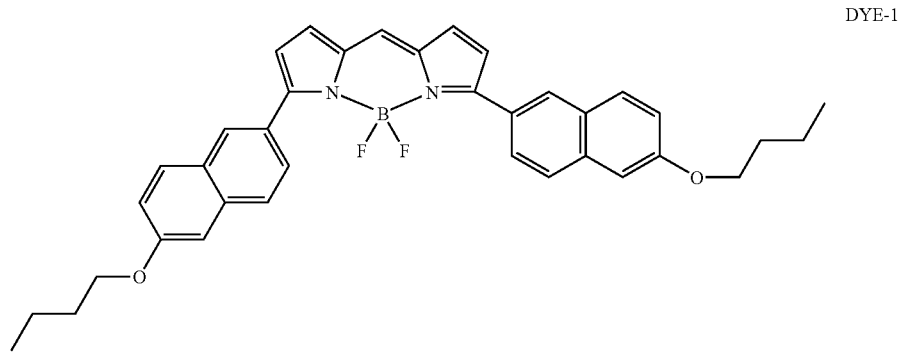

DYE-1

With the solution, a LED was manufactured as described in Example 1.

Figure 4B:
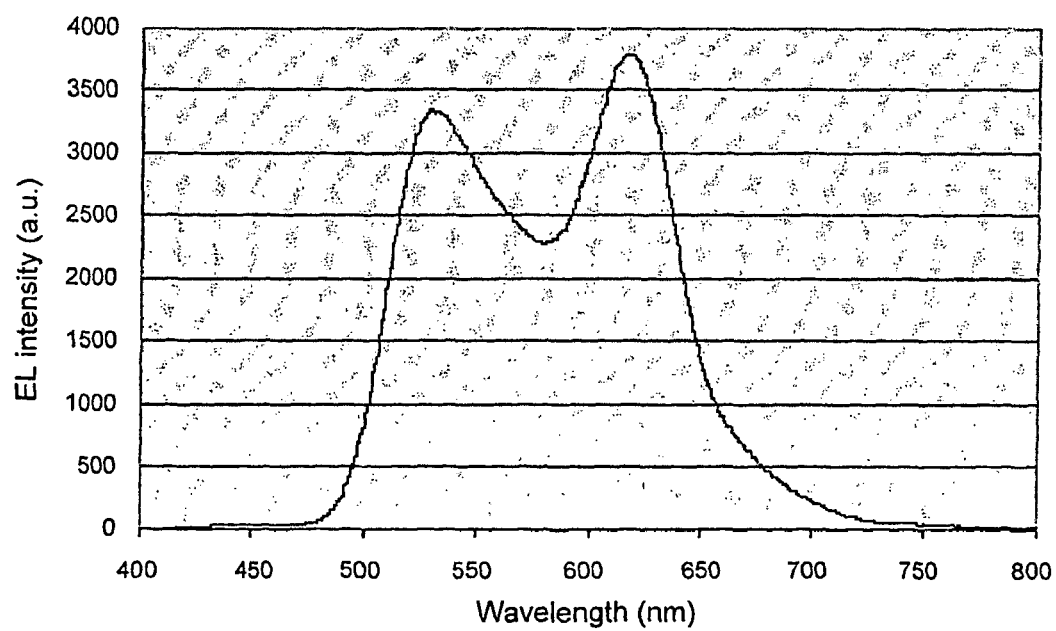

The LED was activated at 4 V and exhibited a $\lambda_{max}$ at 530 nm and at 630 nm. The emission spectrum is shown in FIG. 4B.

EXAMPLE 5

A LED with DYE-1 and Polyfluorene

A solution in toluene was prepared from polyfluorene (as in Example 2) (0.5 wt. %) and DYE-1 (0.005 wt. %)

With the solution, a LED was manufactured as described in Example 1.

Figure 4C:
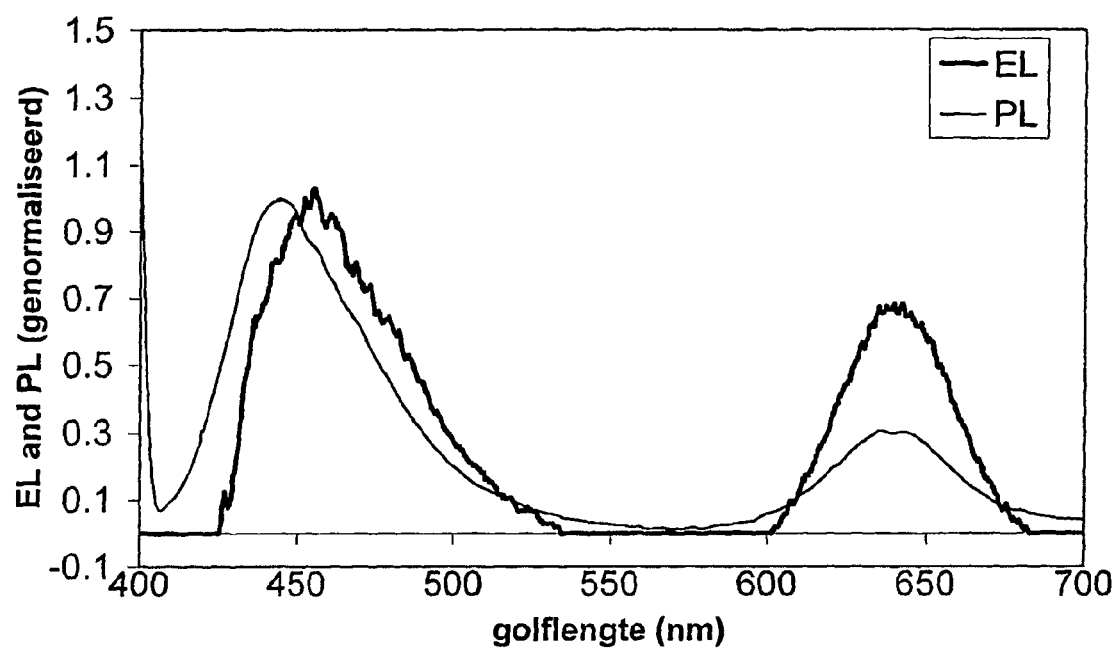

The LED was activated at 4 V and exhibited a $\lambda_{max}$ at ca. 455 nm and at ca. 640 nm. The emission spectrum is represented in FIG. 4C (spectrum EL).

The invention claimed is:

1. A detection system comprising:
a light emitting diode (LED) comprising at least one (semi) conductive electroluminescent active layer comprising at least one electroluminescent organic compound, which at least one electroluminescent organic compound provides for the simultaneous emission of at least two intensity maxima of different wavelengths of light, the simultaneous emission further comprising a reference signal comprising light emitted at a wavelength corresponding to one of the at least two intensity maxima and a detection signal comprising light emitted at a wavelength corresponding to another of the at least two intensity maxima; and
a detector comprising a signal channel configured to detect the detection signal and a separate reference channel configured to simultaneously detect the reference signal in optical communication with the LED,
wherein the at least two different intensity maxima of the different wavelengths are emitted by a first and a second organic electroluminescent compound, wherein the first organic electroluminescent compound has a maximum in the emission spectrum at a different wavelength than the second compound.

2. The detection system according to claim 1, wherein the LED comprises an electroluminescent compound selected from a group consisting of electroluminescent polymers, electroluminescent oligomeric dyes and electroluminescent single dyes.

3. The detection system according to claim 1, wherein the first organic electroluminescent compound is an electroluminescent polymer and the second organic electroluminescent compound is an electroluminescent single dye.

4. The detection system according to claim 1, wherein the emission spectrum of the LED is bimodal.

5. The detection system according to claim 1, wherein the difference in wavelength between two consecutive maxima in the emission spectrum of the LED is at least 40 nm.

6. The detection system according to claim 1, wherein the LED's emission spectrum has at least one maximum, preferably at least two maxima, in the wavelength range of 190-1500 nm, preferably of 400-800 nm.

7. The detection system according to claim 1, wherein the intensity ratio between two consecutive maxima in the emission spectrum is in the range of 0.5 to 1.

8. The detection system according to claim 1, wherein in the emission spectrum the peak to valley ratio of the first and the second maximum is at least 2.

9. The detection system of claim 1 wherein the detector comprises at least one photodiode for each of said channels.

10. The detection system of claim 9, wherein the photodiodes are polymeric photodiodes.

11. The detection system of claim 1, wherein the detection system comprises a sample portion in which or on which a sample is present during detection, which sample portion comprises a coating which is capable of interacting with a component to be measured, so that an absorption property, a fluorescence property or a refractive index of the coating changes upon interaction.

12. The detection system of claim 11, wherein the coating is suitable for interacting with a component selected from the group of polar vapors, non-polar vapors, $CO_2$ and ammonia.

13. The detection system according claim 1, wherein at least one electroluminescent compound is selected from a group consisting of poly(paraphenylene vinylene) compounds, polyfluorene compounds, copolymers of said polymers and polymers derivatized with one or more of said electroluminescent dyes.

14. The detection system according to claim 1, wherein the detection system is a miniaturized sensor system.

15. A detection system comprising:
a light emitting diode (LED) comprising at least one (semi) conductive electroluminescent active layer comprising at least one electroluminescent organic compound, which at least one electroluminescent organic compound provides for the simultaneous emission of at least two intensity maxima of different wavelengths of light, the simultaneous emission further comprising a reference signal comprising light emitted at a wavelength corresponding to one of the at least two intensity maxima and a detection signal comprising light emitted at a wavelength corresponding to another of the at least two intensity maxima; and a detector comprising a signal channel configured to detect the detection signal and a separate reference channel configured to simultaneously detect the reference signal in optical communication with the LED, wherein the at least two different intensity maxima of the different wavelengths are emitted by one organic electroluminescent compound.

16. The detection system according to claim 15, wherein the compound is selected from a group consisting of copolymers having at least two different electroluminescent segments, electroluminescent polymers derivatized with at least one electroluminescent dye, and non-electroluminescent compounds, derivatized with at least two different electroluminescent dyes.

17. The detection system according to claim 15, wherein the LED comprises an electroluminescent compound selected from a group consisting of electroluminescent polymers, electroluminescent oligomeric dyes and electroluminescent single dyes.

18. The detection system according to claim 15, wherein the LED's emission spectrum has at least one maximum, preferably at least two maxima, in the wavelength range of 190-1500 nm, preferably of 400-800 nm.

19. The detection system according to claim 15, wherein the intensity ratio between two consecutive maxima in the emission spectrum is in the range of 0.5 to 1.

20. The detection system according to claim 15, wherein in the emission spectrum the peak to valley ratio of the first and the second maximum is at least 2.

21. The detection system of claim 15, wherein the detector comprises at least one polymeric photodiode for each of said channels.

22. The detection system of claim 15, wherein the detection system comprises a sample portion in which or on which a sample is present during detection, the sample portion comprising a coating which is capable of interacting with a component to be measured, so that an absorption property, a fluorescence property or a refractive index of the coating changes upon interaction and wherein the coating is suitable for interacting with a component selected from the group of polar vapors, non-polar vapors, $CO_2$ and ammonia.

23. The detection system of claim 15, wherein the electroluminescent compound is an electroluminescent polymer selected from a group consisting of polyfluorene compounds, poly(paraphenylene vinylene) compounds, polyfluorene compounds, copolymers of said polymers and polymers derivatized with one or more electroluminescent dyes; or an electroluminescent polymer from a group consisting of polyacetylene compounds, polythiophene compounds, polypyrroles, polyanilines and copolymers of these polymers.

24. A detection system comprising:
a light emitting diode (LED) comprising at least one (semi) conductive electroluminescent active layer comprising at least one electroluminescent organic compound, which at least one electroluminescent organic compound provides for the simultaneous emission of at least two intensity maxima of different wavelengths of light, the simultaneous emission further comprising a reference signal comprising light emitted at a wavelength corresponding to one of the at least two intensity maxima and a detection signal comprising light emitted at a wavelength corresponding to another of the at least two intensity maxima; and
a detector comprising a signal channel configured to detect the detection signal and a separate reference channel configured to simultaneously detect the reference signal in optical communication with the LED,
wherein at least one electroluminescent compound is selected from a group consisting of polyfluorene compounds, copolymers of said polyflorene compounds and polymers derivatized with one or more electroluminescent dyes.

25. A detection system comprising:
a light emitting diode (LED) comprising at least one (semi) conductive electroluminescent active layer comprising at least one electroluminescent organic compound, which at least one electroluminescent organic compound provides for the simultaneous emission of at least two intensity maxima of different wavelengths of light, the simultaneous emission further comprising a reference signal comprising light emitted at a wavelength corresponding to one of the at least two intensity maxima and a detection signal comprising light emitted at a wavelength corresponding to another of the at least two intensity maxima; and
a detector comprising a signal channel configured to detect the detection signal and a separate reference channel configured to simultaneously detect the reference signal in optical communication with the LED,
wherein the light emitting diode and the detector are present on or in a carrier material, wherein the carrier material is flexible.

26. The detection system according to claim 25, wherein the LED comprises an electroluminescent compound selected from a group consisting of electroluminescent polymers, electroluminescent oligomeric dyes and electroluminescent single dyes.

27. The detection system according to claim 25, wherein the LED's emission spectrum has at least one maximum, preferably at least two maxima, in the wavelength range of 190-1500 nm, preferably of 400-800 nm.

28. The detection system according to claim 25, wherein the intensity ratio between two consecutive maxima in the emission spectrum is in the range of 0.5 to 1.

29. The detection system according to claim 25, wherein in the emission spectrum the peak to valley ratio of the first and the second maximum is at least 2.

30. The detection system of claim 25, wherein the detector comprises at least one polymeric photodiode for each of said channels.

31. The detection system of claim 25, wherein the detection system comprises a sample portion in which or on which a sample is present during detection, the sample portion comprising a coating which is capable of interacting with a component to be measured, so that an absorption property, a fluorescence property or a refractive index of the coating changes upon interaction and wherein the coating is suitable for interacting with a component selected from the group of polar vapors, non-polar vapors, $CO_2$ and ammonia.

32. The detection system of claim 25, wherein the electroluminescent compound is an electroluminescent polymer selected from a group consisting of polyfluorene compounds, poly(paraphenylene vinylene) compounds, polyfluorene compounds, copolymers of said polymers and polymers derivatized with one or more electroluminescent dyes; or an electroluminescent polymer from a group consisting of polyacetylene compounds, polythiophene compounds, polypyrroles, polyanilines and copolymers of these polymers.

33. A detection system comprising:
a light emitting diode (LED) comprising at least one (semi) conductive electroluminescent active layer comprising at least one electroluminescent organic compound, which at least one electroluminescent organic compound provides for the simultaneous emission of at least two intensity maxima of different wavelengths of light, the simultaneous emission further comprising a reference signal comprising light emitted at a wavelength corresponding to one of the at least two intensity maxima and a detection signal comprising light emitted at a wavelength corresponding to another of the at least two intensity maxima; and a detector comprising a signal channel configured to detect the detection signal and a separate reference channel configured to simultaneously detect the reference signal in optical communication with the LED, wherein at least one electroluminescent compound is selected from the group of polyacetylene compounds, polythiophene compounds, polypyrroles, polyanilines and copolymers of these polymers.

\* \* \* \* \*